United States Patent
Ouchi et al.

(10) Patent No.: US 8,179,932 B2
(45) Date of Patent: *May 15, 2012

(54) PULSE LASER APPARATUS, TERAHERTZ MEASURING APPARATUS, AND TERAHERTZ TOMOGRAPHIC APPARATUS

(75) Inventors: Toshihiko Ouchi, Sagamihara (JP); Takashi Katagiri, Sendai (JP); Kentaro Furusawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/093,804

(22) Filed: Apr. 25, 2011

(65) Prior Publication Data

US 2011/0210252 A1   Sep. 1, 2011

Related U.S. Application Data

(63) Continuation of application No. 12/354,716, filed on Jan. 15, 2009, now Pat. No. 7,953,130.

(30) Foreign Application Priority Data

Jan. 29, 2008 (JP) .................................. 2008-017842

(51) Int. Cl.
    *H01S 3/067* (2006.01)
(52) U.S. Cl. ............. 372/25; 372/6; 372/21; 359/337.2; 359/337.5; 359/341.1
(58) Field of Classification Search ................ 372/6, 21, 372/22, 25; 359/341.1, 337.2, 337.5
See application file for complete search history.

(56) References Cited

U.S. PATENT DOCUMENTS

| | | | | |
|---|---|---|---|---|
| 5,155,621 A * | 10/1992 | Takeda et al. | ................. | 359/337 |
| 5,880,877 A | 3/1999 | Fermann et al. | .............. | 359/341 |
| 5,892,615 A * | 4/1999 | Grubb et al. | ............. | 359/341.31 |
| 6,181,463 B1 | 1/2001 | Galvanauskas et al. | ...... | 359/330 |
| 7,224,518 B2 * | 5/2007 | Tauser et al. | ................ | 359/337.5 |
| 7,557,588 B2 | 7/2009 | Ouchi et al. | ................. | 324/637 |
| 7,560,695 B2 | 7/2009 | Kasai et al. | ................ | 250/338.4 |
| 7,564,034 B2 | 7/2009 | Ouchi | .......................... | 250/340 |
| 7,745,791 B2 | 6/2010 | Kasai et al. | ................ | 250/341.1 |
| 7,782,067 B2 | 8/2010 | Ouchi et al. | ................. | 324/637 |
| 7,953,130 B2 * | 5/2011 | Ouchi et al. | .................... | 372/25 |
| 2003/0178584 A1 | 9/2003 | Arnone et al. | ............. | 250/495.1 |
| 2004/0095147 A1 | 5/2004 | Cole | ............................. | 324/629 |
| 2004/0190119 A1 | 9/2004 | Tauser et al. | ................. | 359/333 |
| 2005/0168805 A1 | 8/2005 | Aiso | .......................... | 359/341.1 |

(Continued)

FOREIGN PATENT DOCUMENTS

JP    4-291972    10/1992

(Continued)

*Primary Examiner* — Jessica Stultz
*Assistant Examiner* — Michael Carter
(74) *Attorney, Agent, or Firm* — Fitzpatrick, Cella, Harper & Scinto

(57) ABSTRACT

A pulse laser apparatus includes a laser configured to generate a pulse of a laser beam, a fiber amplifier, and a pulse compressor. The fiber amplifier includes a rare-earth doped fiber that exhibits normal dispersion at a wavelength of the laser beam generated from the laser. The pulse laser apparatus further includes a unit configured to give a loss to energy portions in a wavelength region corresponding to a zero-dispersion wavelength of the rare-earth doped fiber and/or a wavelength region longer than the zero-dispersion wavelength within a wavelength spectrum of the laser beam having been chirped in the fiber amplifier.

14 Claims, 16 Drawing Sheets

U.S. PATENT DOCUMENTS

| | | | |
|---|---|---|---|
| 2006/0214176 A1 | 9/2006 | Ouchi et al. | 257/98 |
| 2006/0227340 A1 | 10/2006 | Shioda et al. | 356/614 |
| 2006/0237650 A1 | 10/2006 | Taday | 250/339.11 |
| 2006/0244629 A1 | 11/2006 | Miyazaki et al. | 340/855.7 |
| 2006/0291036 A1 | 12/2006 | Shukunami et al. | 359/333 |
| 2007/0030115 A1 | 2/2007 | Itsuji et al. | 340/5.8 |
| 2007/0195921 A1 | 8/2007 | Ouchi | 378/1 |
| 2007/0229094 A1 | 10/2007 | Kasai et al. | 324/639 |
| 2008/0048792 A1 | 2/2008 | Ouchi et al. | 331/107 |
| 2008/0314152 A1 | 12/2008 | Ouchi | 73/597 |
| 2009/0056455 A1 | 3/2009 | Ouchi | 73/643 |
| 2009/0059226 A1 | 3/2009 | Kajiki et al. | 356/328 |
| 2009/0198466 A1 | 8/2009 | Kajiki et al. | 702/85 |

FOREIGN PATENT DOCUMENTS

| | | |
|---|---|---|
| JP | 6-088976 | 3/1994 |
| JP | 2711778 | 2/1998 |
| JP | 3811564 | 8/2006 |
| JP | 2006-526774 | 11/2006 |
| JP | 2007-516600 | 6/2007 |

\* cited by examiner

PULSE LASER APPARATUS, TERAHERTZ MEASURING APPARATUS, AND TERAHERTZ TOMOGRAPHIC APPARATUS

This application is a continuation of application Ser. No. 12/354,716, filed Jan. 15, 2009 now U.S. Pat. No. 7,953,130, now allowed, the contents of which are incorporated by reference herein.

BACKGROUND OF THE INVENTION

1. Field of the Invention

The present invention relates to an ultrashort pulse laser apparatus using an optical fiber, and to a terahertz measuring apparatus using, as an excitation light source, a laser beam emitted from the ultrashort pulse laser apparatus.

2. Description of the Related Art

Recently, a nondestructive sensing technique has been developed which employs electromagnetic waves (30 GHz to 30 THz; hereinafter referred to simply as "THz" waves) ranging from a millimeter wave to a terahertz (THz) wave. An imaging technique to realize a safe seeing-through apparatus instead of an X-ray fluoroscope has been developed as one application field of the electromagnetic waves in such a frequency band. As other application fields, there have also been developed a spectroscopic technique of measuring an absorption spectrum and a complex permittivity inside a substance to examine the coupling state, etc., a technique of analyzing biological molecules, and a technique of evaluating a carrier density and mobility.

In view of the importance in nondestructively performing a quality check in a production line of a factory, for example, applications to inspection of defects and/or foreign substances in moldings, and inspection of components, foreign substances and/or defects in chemical substances, etc. have also been studied. In those applications, a tomographic image can be taken by utilizing transmissivity of the THz waves. The chemical substances include, for example, inks such as pigments and dyes, toner, medicines, cosmetics, and paints. As an example of the inspection apparatus, Japanese Patent Laid-Open (Translation of PCT Application) No. 2006-526774 discloses an apparatus that is applied to the inspection of medicines by using THz-TDS (Time Domain Spectroscopy). With the disclosed apparatus, the kinds of materials inside medicines, for example, can be analyzed on the basis of spectrum information in the THz-wave region.

In the THz-TBS, as disclosed in Japanese Patent Laid-Open (Translation of PCT Application) No. 2006-526774, an excitation light source for generating and detecting THz, waves is required which has a pulse width of about 100 femtosecond (fs) or less. A pulse laser using a titanium-sapphire crystal, for example, is preferably used as the excitation light source.

Such a laser using a solid crystal is advantageous in increasing an output, but it is not satisfactory in output stability and productivity. Further, that laser is very expensive. As a practical light source, therefore, the use of a fiber laser is studied.

The fiber laser is advantageous in that a very stable fiber amplifier can be used as a gain medium and a size can be reduced because of no necessity of constructing a spatial optical system. In addition, stability can be increased because the number of parts requiring adjustment of an optical axis is greatly reduced, and the cost can be reduced because productivity is increased.

The excitation light source used for the THz-TDS is required to have an average optical output of not smaller than several tens mW, desirably not smaller than 100 mW. It is difficult to constitute the fiber laser having such a high output and ultrashort pulse by using only a fiber oscillator. Therefore, that type of fiber laser is usually realized by connecting an output of an oscillator, which emits a seed light, to an external fiber amplifier and an external fiber compressor. As an example of the related art, Japanese Patent No. 2711778 describes an apparatus in which, after amplifying a seed light by a rare-earth doped fiber amplifier with normal dispersion, a pulse is shortened with dispersion compensation by using an anomalous dispersion fiber. Further, Japanese Patent No. 3811564 describes an apparatus in which a seed light is amplified by a rare-earth doped fiber amplifier with anomalous dispersion, while a pulse is shortened on the basis of a nonlinear effect with the Raman soliton compression.

It cannot be said, however, that the fiber laser used at present has an output sufficient to increase an output of the THz waves and to widen a Fourier frequency band for the purpose of enhancing an analysis ability of a THz-TDS measuring apparatus. In other words, when the band of a THz spectrum is to be expanded to 10 THz or above, an ultrashort pulse of approximately 10 fs is required as the width of a laser pulse in an optical domain. Up to now, however, it has been difficult to realize a fiber laser having an output of not smaller than 100 mW and outputting such an ultrashort pulse.

With the apparatus described in the above-cited Japanese Patent No. 2711778, when the amplified pulse has a large peak value, the anomalous dispersion fiber used as a dispersion compensation fiber may distort a pulse wavelength due to the nonlinear effect, thus causing phase noise and Raman scattering. In other words, there has been a room for a further improvement in the practical excitation light source for the THz-TDS. For such an improvement, as described in the above-cited Japanese Patent No. 2711778, a peak value of the pulse is reduced by suppressing an optical output with an attenuator, or by increasing a chirp amount by using a fluorinated-Er doped fiber to provide larger normal dispersion. This is because an ordinary quartz fiber, which is not fluorinated, has a limitation in an amount of dispersion shift. However, when the fluorinated fiber is used, a difficulty arises in stably fusing those fibers with each other for coupling between them. Such a difficulty cancels the advantages of reducing spatial joints, cutting the cost, and increasing stability, which are specific to the fiber laser.

On the other hand, the apparatus described in the above-cited Japanese Patent No. 3811564 employs, as a quartz fiber, an erbium-doped fiber amplifier in an anomalous dispersion region that is relatively easily realized, and utilizes the Raman soliton nonlinear compression. According to such an arrangement, however, as an output increases, a wavelength shift based on a Raman shift is increased and it becomes more difficult to suppress a side lobe, i.e., a pedestal, in a time-dependent waveform. When the THz waves are generated by using a photoconductive device or a nonlinear crystal, the occurrence of a shift of the central wavelength from the design value raises a problem of reducing conversion efficiency and causes noise, which is not desired for the measurement using the IDS, due to THz waves generated by the presence of a pedestal.

One conceivable solution to those problems is to provide small normal dispersion by using an ordinary quartz fiber and to perform compression in a downstream stage. However, when the chirp amount is increased, namely when the fiber length is increased, to overcome the problems with the apparatus described in the above-cited Japanese Patent No. 2711778, energy of the chirped light extends up to a zero-dispersion wavelength region, thus causing an undesired nonlinear effect, e.g., a four-wave mixing. Further, when the optical output increases, induced Raman scattering occurs in the longer wavelength side. As a result, a pedestal is generated in a time-dependent waveform after the compression.

SUMMARY OF THE INVENTION

Accordingly, an exemplary embodiment of the present invention provides a pulse laser apparatus which generates a low pedestal or a reduced pedestal.

According to one exemplary embodiment of the present invention, there is provided a pulse laser apparatus including a laser configured to generate a pulse of a laser beam, a fiber amplifier, and a pulse compressor, wherein the fiber amplifier includes a rare-earth doped fiber that exhibits normal dispersion at a wavelength of the laser beam generated from the laser, and the pulse laser apparatus further includes a unit configured to give a loss to energy portions in a wavelength region corresponding to a zero-dispersion wavelength of the rare-earth doped fiber and/or a wavelength region longer than the zero-dispersion wavelength within a wavelength spectrum of the laser beam having been chirped in the fiber amplifier.

According to another exemplary embodiment of the present invention, there is provided a terahertz pulse generating apparatus including a photoconductive device or a nonlinear crystal, and the above-mentioned pulse laser apparatus, wherein a terahertz pulse is generated by irradiating the laser beam from the pulse laser apparatus to the photoconductive device or the nonlinear crystal.

According to still another exemplary embodiment of the present invention, there is provided a terahertz measuring apparatus including the above-mentioned pulse laser apparatus, and a branch unit arranged to branch an optical output of the pulse laser apparatus into two parts, wherein one part of the optical output is irradiated to a first photoconductive device or a first nonlinear crystal to generate a terahertz pulse, and the other part of the optical output is irradiated to a second photoconductive device or a second nonlinear crystal such that the second photoconductive device or the second nonlinear crystal operates as a detector, thus performing terahertz time domain spectroscopy in accordance with pump-probe measurement.

According to still another exemplary embodiment of the present invention, there is provided a terahertz tomographic apparatus, wherein internal tomographic image data of a specimen is obtained by measuring a reflected pulse from the specimen with the above-mentioned terahertz measuring apparatus, and an internal tomographic image is output to an output unit on the basis of the obtained data.

According to still another exemplary embodiment of the present invention, there is provided a method of using the pulse laser apparatus, wherein the method comprises irradiating the laser beam from the pulse laser apparatus to a photoconductive device or a nonlinear crystal to generate a terahertz pulse.

With the pulse laser apparatus according to the exemplary embodiment of the present invention, the generated laser beam has a pulse width of 20 fs or less and an average output of 200 mW or more, and the pulse of the laser beam having a low pedestal in a time-dependent waveform of the pulse can be realized. Further, a satisfactory terahertz measuring apparatus can be provided by using, as a light source, the pulse laser apparatus according to the exemplary embodiment of the present invention.

Further features of the present invention will become apparent from the following description of the exemplary embodiments with reference to the attached drawings.

DESCRIPTION OF THE EMBODIMENTS

Figure 1:
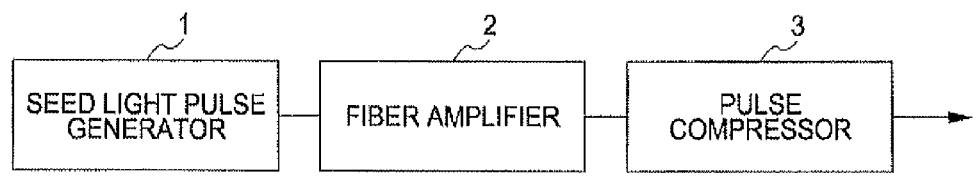
FIG. 1 is a block diagram of a pulse laser apparatus according to an exemplary embodiment of the present invention.

As shown in FIG. 1, a pulse laser apparatus according to an exemplary embodiment of the present invention includes a laser unit (seed light pulse generator) 1, a fiber amplifier 2, and a pulse compressor 3.

The fiber amplifier 2 is constituted by a rare-earth doped fiber, which exhibits normal dispersion at a wavelength of a laser beam emitted from the laser unit 1.

The pulse laser apparatus further includes a unit for giving a loss to an energy portion in a wavelength region corresponding to a zero-dispersion wavelength of the rare-earth doped fiber within a wavelength spectrum of the laser beam, which has been chirped in the fiber amplifier 2.

Alternatively, the pulse laser apparatus further includes a unit for giving a loss to an energy portion in a wavelength region longer than the zero-dispersion wavelength.

Of course, the pulse laser apparatus can include a unit for giving a loss to energy portions in both the zero-dispersion wavelength region and the wavelength region longer than the zero-dispersion wavelength.

Such an arrangement can give a loss to the energy portions in the wavelength region equal to or longer than the zero-dispersion wavelength, or can cut those energy portions. Therefore, when dispersion compensation is performed in the pulse compressor 3, a light pulse can be obtained in such a state that a pedestal is reduced or the occurrence of a pedestal is suppressed.

An example of the unit for giving a loss to the energy portions of the laser beam in the wavelength region equal to or longer than the zero-dispersion wavelength is a wavelength filter. Alternatively, the loss giving unit can be provided by forming a bent portion at least in a part of the rare-earth doped fiber so as to generate a leakage loss in the wavelength region equal to or longer than the zero-dispersion wavelength. Alternatively, the loss giving unit can also be realized by constituting at least a part of the rare-earth doped fiber as a fiber having a W-shaped sectional refractive-index profile.

The loss giving unit serves to suppress higher-order nonlinear effects (such as a phenomenon of four-wave mixing and induced Raman scattering), which occur during propagation of the laser beam through the rare-earth doped fiber, by giving a loss to the energy portions of the laser beam in the wavelength region equal to or longer than the zero-dispersion wavelength.

The laser beam generated from the pulse laser apparatus is desirably set to have a pulse width of 20 fsec or less and an average output of 200 mW or more, for example.

As another desired modification, the curvature of the above-described bent portion can be made variable by providing a unit that is able to adjust the curvature of the bent portion while monitoring the waveform.

As described later in exemplary embodiments, a terahertz pulse can be generated by using the pulse laser apparatus described above. More specifically, a terahertz pulse can be generated by preparing a photoconductive device or a nonlinear crystal and irradiating the laser beam from the pulse laser apparatus to the photoconductive device or the nonlinear crystal. A terahertz pulse generating apparatus can be provided in such a way.

Further, a branch portion can be prepared in addition to the pulse laser apparatus. The optical output of the pulse laser apparatus is branched into two parts by the branch portion. One part of the optical output is irradiated to the photoconductive device or the nonlinear crystal to generate a terahertz pulse. The other optical output is irradiated to a second photoconductive device or a second nonlinear crystal such that the second photoconductive device or the second nonlinear crystal operates as a detector, thereby performing terahertz time domain spectroscopy in accordance with pump-probe measurement. A terahertz measuring apparatus can be provided in such a way. In that terahertz measuring apparatus, the light beam irradiated to the second photoconductive device or the second nonlinear crystal can be obtained by passing the laser beam output from the pulse laser apparatus through a higher-harmonic generator, and by using the light that has passed through the higher-harmonic generator.

Further, a terahertz tomographic apparatus can be provided by measuring a pulse, which is reflected from a specimen, with the terahertz measuring apparatus to obtain internal sectional image data of the specimen, and by outputting an internal sectional image to an output unit on the basis of the obtained data.

The pulse laser apparatus, the terahertz pulse generating apparatus, the terahertz measuring apparatus, and the terahertz tomographic apparatus will be described one by one with reference to the drawings.

The pulse laser apparatus according to the exemplary embodiment of the present invention is first described.

FIG. 1 is a block diagram illustrating a general configuration of the pulse laser apparatus.

The seed light pulse generator 1 is desirably a soliton laser constructed in the form of a ring by using a fiber amplifier. Another type of femtosecond laser can also be used. Herein, a soliton laser having an oscillation wavelength of 1558 nm, a repetition rate of about 40 MHz, a pulse width of 320 ns, and an average output of about 4 mW is employed.

The optical output of the seed light pulse generator 1 is introduced to enter the fiber amplifier 2, according to the exemplary embodiment of the present invention, through coupling with fiber fusion or a lens (not shown). An output of the fiber amplifier 2 is introduced to the pulse compressor 3 which is constituted by a fiber or a spatial system. The pulse compressor 3 shapes the output of the fiber amplifier 2 and outputs a light pulse having a higher optical output and a narrower pulse width than the seed light pulse.

Figure 2:
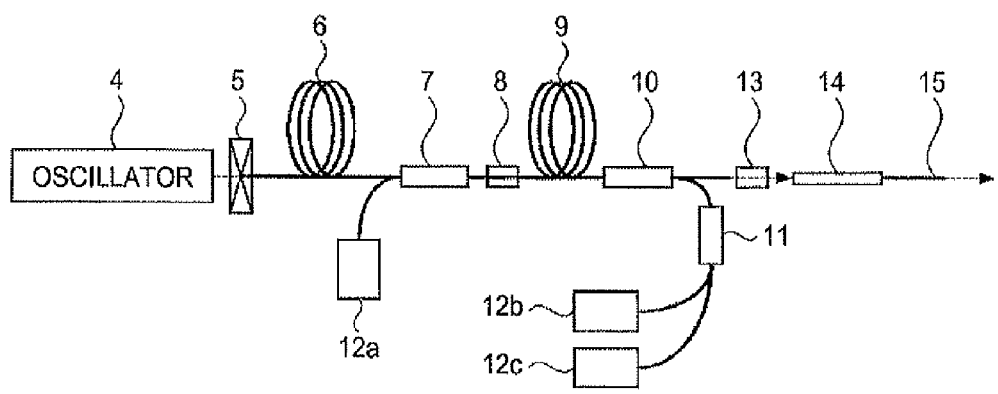
FIG. 2 illustrates a detailed configuration of the pulse laser apparatus, particularly a fiber amplifier, according to the exemplary embodiment of the present invention.

Details of the pulse laser apparatus, particularly the fiber amplifier, will be described below with reference to FIG. 2 and subsequent drawings. An oscillator 4 in FIG. 2 corresponds to the seed light generator 1 in FIG. 1. In order to couple an output of the oscillator 4 to a fiber through a spatial system, a ½ wavelength plate 5 is inserted to adjust the direction of polarization. For the coupling of the output, a single-mode quartz fiber (SMF) 6 of the polarization maintaining type is used which includes a collimator lens (e.g., of the pig tail type), though not shown. Further, the laser pulse is propagated to an erbium (Er) doped fiber (EDF) 9 through a WDM (wavelength division multiplex) coupler 7 and a polarization controller 8 and is amplified by the erbium doped fiber 9. The amplified laser pulse is output through another WDM coupler 10 and is coupled to the pulse compressor, which includes later-described fibers 14 and 15, through an isolator 13.

Outputs of three 1.48-μm LIDS 12a to 12c with a high power (400 mW), each serving as the excitation light source, are injected to the erbium doped fiber 9 through WDM couplers 7 and 10. The outputs of the LDs 12b and 12c are injected after they have been coupled to each other through a polarization maintaining coupler 11.

Table 1, given below, lists the specifications of the two fibers 6 and 9 used herein. Other fibers used in coupler portions, etc. also have the single mode, but the length of each fiber is held as short as possible (about several centimeters).

TABLE 1

| | Secondary Group Velocity Dispersion $\beta_2$ | Mode Field Diameter MFD | Nonlinear Coefficient $\gamma$ |
|---|---|---|---|
| SMF 6 | −21.4 ps$^2$/km | 9.3 µm | 1.89 w$^{-1}$ km$^{-1}$ |
| EDF 9 | 6.44 ps$^2$/km | 8.0 µm | 2.55 w$^{-1}$ km$^{-1}$ |

Thus, the single-mode fiber disposed in an input stage exhibits anomalous dispersion and has a role to chirp (pre-chirp) the input pulse with negative dispersion. On the other hand, the erbium doped fiber 9 exhibits low normal dispersion and causes a wavelength chirp with the normal dispersion on the basis of self-phase modulation (SPM) while performing optical amplification. The lengths of the SMF 6 and the EDF 9 are set to 4.5 m and 6 m herein, respectively, but their practical lengths are not limited to those values.

The polarization controller 8 is adjusted such that the output of the fiber amplifier is maximized. A part of the output can be monitored for feedback control so as to ensure the stable output at all times.

Behaviors of the fiber amplifier in the wavelength region, in which it performs the optical amplification, will be described below with reference to FIG. 3.

Figure 3:
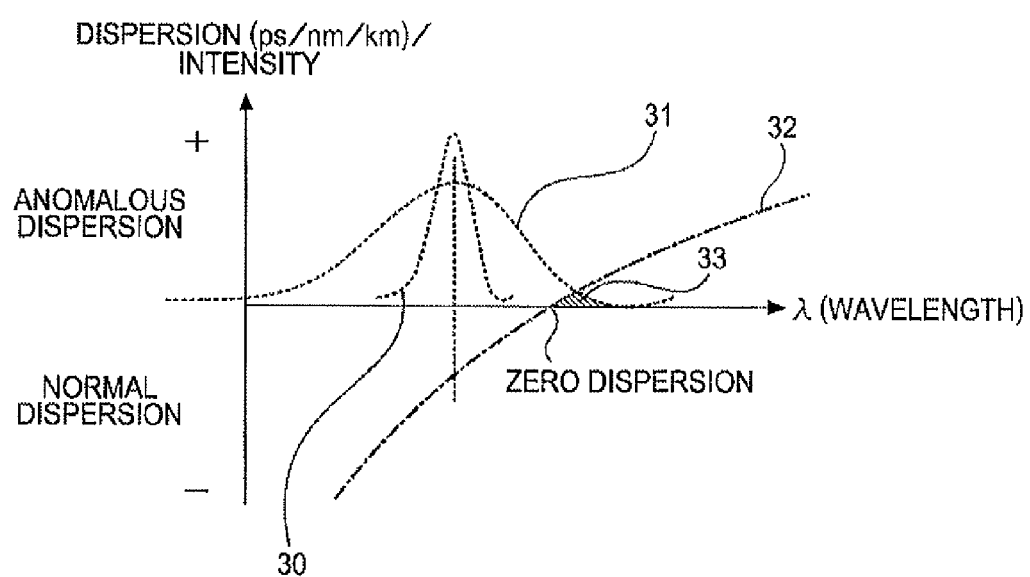
FIG. 3 is a graph representing a dispersion state of the fiber amplifier.

FIG. 3 is a graph representing, in a superimposed manner, dependency of a fiber dispersion amount upon wavelength (indicated by a dispersion curve 32) and the spectral intensity of the light pulse. The erbium doped fiber used in the exemplary embodiment of the present invention is formed by causing a dispersion shift in a quartz fiber to provide normal dispersion such that the dispersion compensation can be easily performed in the pulse compressor. As seen from FIG. 3, the erbium doped fiber exhibits low normal dispersion at a center wavelength of the spectrum of an incident pulse 30. After the amplification, the incident pulse 30 turns to a chirped pulse having a spectrum, indicated by 31, as a result of undergoing an increase of power and a chirp of wavelength, such that optical energy spreads up to a zero-dispersion wavelength region of the fiber and an anomalous dispersion region (indicated by a hatched portion 33). Because of the occurrence of various nonlinear effects, the optical energy in those regions is subjected to wavelength conversion to such an extent as not sufficiently compensated for by the pulse compressor in the downstream stage, or such an extent as generating a pedestal in the time-dependent waveform.

Figure 4A:
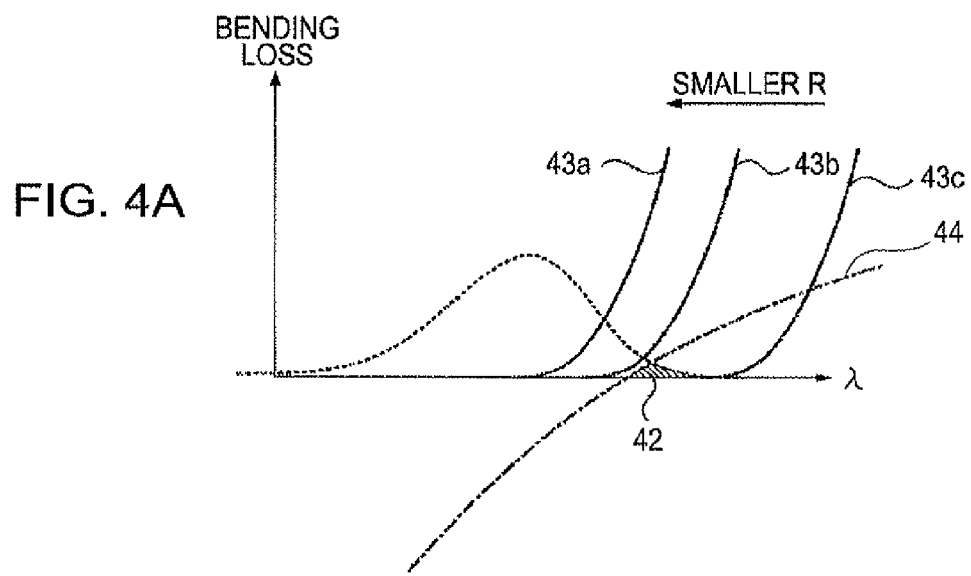
FIG. 4A is a graph and FIG. 4B is a schematic view, each illustrating the filter function of the fiber amplifier.
Figure 4B:

Those problems can be avoided by effectively removing the optical energy distributing over wavelengths equal to or longer than the zero-dispersion wavelength (i.e., the anomalous dispersion region 33 in the graph of FIG. 3). FIGS. 4A and 4B illustrate an exemplary embodiment for effectively removing that optical energy.

An erbium doped fiber 41 used herein exhibits different propagation characteristics at longer wavelengths depending on a curvature radius R when the fiber is wound around a bobbin 40, as shown in FIG. 4B. The reason is that bending of the fiber changes conditions for total reflection in the longer wavelength side and raises a limitation in wavelength at which the optical energy can propagate. FIG. 4A illustrates such a limitation. As seen from FIG. 4A, as the curvature radius R becomes smaller, the wavelength at which the bending loss increases significantly shifts gradually toward the shorter wavelength side as indicated by 43c, 43b and 43a. In FIG. 4A, numerals 42 and 44 denote an anomalous dispersion region and a dispersion curve, respectively. In the exemplary embodiment of the present invention, the curvature radius at which the erbium doped fiber is wound is adjusted to a value (e.g., R=3.5 cm), as indicated by 43b, so that the optical energy in the wavelength region longer than the zero-dispersion wavelength is not leaked to be output from the fiber. As a result, the undesired nonlinear effects can be prevented and an ultrashort pulse having a smaller pedestal after the compression can be generated.

Figure 5:
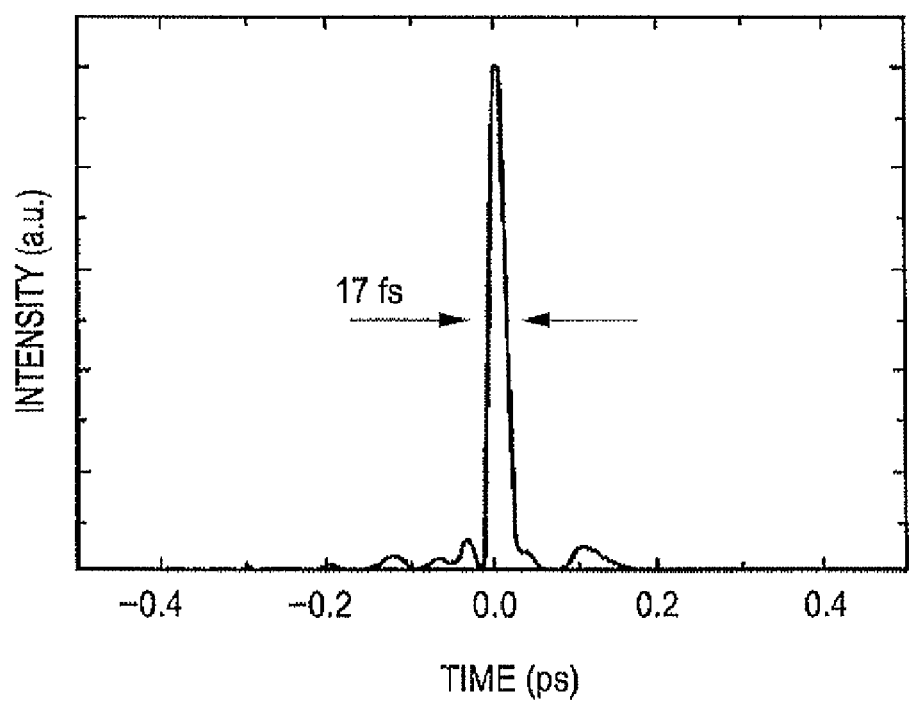
FIG. 5 is a graph representing an example of a pulse laser output in the exemplary embodiment of the present invention.

In the exemplary embodiment, the optical output of about 400 mW is obtained from the fiber amplifier, and after the compression, a light pulse with an output of about 200 mW and a half-value breadth 17 fs (see FIG. 5) obtained at 1558 nm. The pulse compressor 3 is constituted by a combination of a large-diameter photonic crystal fiber 14 and a highly nonlinear fiber 15.

As fiber parameters, the photonic crystal fiber 14 has the secondary group velocity dispersion of −30.3 ps$^2$/km, the mode field diameter of 26 µm, the nonlinear coefficient of 0.182 W$^{-1}$m$^{-1}$, and the length of 42 cm. The highly nonlinear fiber 15 has the secondary group velocity dispersion of −14.6 ps$^2$/km, the nonlinear coefficient of 4.53 W$^{-1}$km$^{-1}$, and the length of 1.5 cm. Such a construction of the pulse compressor 3 is merely one example. As another example, the dispersion compensation can also be spatially performed by using, e.g., a diffraction grating.

While the erbium doped fiber is employed as the fiber of the fiber amplifier, a fiber doped with another rare-earth element, such as thulium Tm or ytterbium Yb, can also be used.

With the above-described construction, the fiber amplifier performs the wavelength chirp and the optical amplification of the incident light pulse with the normal dispersion on the basis of the SPM. Further, the optical energy in the wavelength region equal to or longer than zero-dispersion wavelength can be removed by utilizing the fiber bending loss. Therefore, a light pulse of 20 fs having a small pedestal can be obtained even when the pulse is shortened by using the pulse compressor.

In addition to the above-described method, the optical energy in the longer wavelength side can be cut, for example, by using a fiber in which the cutoff frequency can be set by controlling the refractive index into a W-shaped profile, or by inserting a wavelength filter into an output stage. When the fiber having the W-shaped refractive index profile or the wavelength filter is used, it is not always required to control the fiber bending loss.

First Exemplary Embodiment

Figure 6:
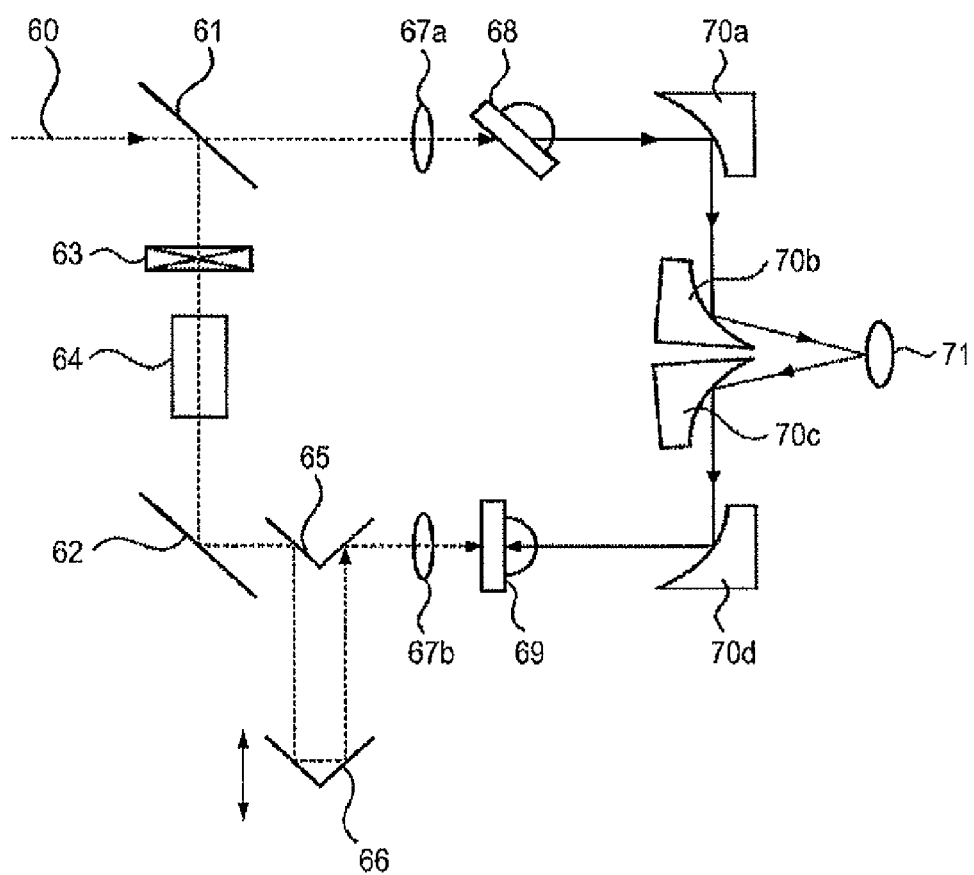
FIG. 6 is a diagram illustrating a configuration of a terahertz TDS measuring apparatus according to a first exemplary embodiment of the present invention.

A THz TDS (Time Domain Spectroscopy) system can be constituted by using the ultrashort pulse laser described above. FIG. 6 is a diagram illustrating a configuration of a terahertz TDS measuring apparatus using the pulse laser apparatus according to a first exemplary embodiment of the present invention. Numeral 60 denotes an output beam of the above-described ultrashort pulse laser including the fiber amplifier, according to the exemplary embodiment of the present invention. The output beam has a wavelength of 1558 nm, an optical output of about 200 mW, and a pulse width of 17 fs. In FIG. 6, dotted lines represent propagation paths of the laser beam, and solid lines represent propagation paths of THz waves. The illustrated apparatus according to the first exemplary embodiment can provide an ultrashort pulse laser of 20 fs or less, having a high output of 100 mW or more and a smaller pedestal in the time domain, which has hitherto been difficult to realize in a femtosecond laser using a fiber amplifier in a light-pulse amplifying section.

The operation of the terahertz TDS measuring apparatus will be described below with reference to FIG. 6. The laser pulse output 60 is divided into two light beams by a wideband half mirror 61. One light beam is irradiated to a photoconductive device 68 through a lens 67a. The lens 67a can be replaced with a parabolic mirror. In such a case, however, the optical system is slightly modified. The photoconductive device 68 employs, as a photoconductive film, an InGaAs epitaxial film that has an absorption in a band of 1550 nm. The photoconductive film is obtained, for example, by doping Be with a density of $1 \times 10^{18}$ cm$^{-3}$ into LT-InGaAs (composition of In-0.53) which is formed through MBE (Molecular Beam Epitaxy) at 200° C., and annealing it in an atmosphere of hydrogen at 600° C. on ex-situ. The photoconductive device 68 is constituted by further forming electrodes, such as dipole antennas, through epitaxy on the surface of an InP substrate. Since the InP substrate is transparent to the light of 1550 nm, the light beam can be introduced to enter the photoconductive device 68 from the substrate side. This is effective in reducing absorption of THz waves caused by phonons within the InP substrate. Of course, as in the known GaAs type, the photoconductive device can also be constituted such that an electric filed is applied to a heterostructure, which is in the form of a PIN-structure, in a direction perpendicular to the film. Further, an electro-optical crystal, such as DAST or InAs, can be used instead of the photoconductive device. While the light beam is introduced to obliquely enter the photoconductive device in FIG. 6 to control a spatial radiation pattern of generated THz waves, it can also be introduced to perpendicularly enter the photoconductive device.

A semispherical structure added to the photoconductive device 68 (including another photoconductive device 69 described below) represents a semispherical lens of Si and serves to efficiently radiate the THz waves, generated from the photoconductive device, to a space. The generated THz waves are collimated by a parabolic mirror 70a and are condensed by a parabolic mirror 70b onto the surface of a specimen 71 to be measured. The THz waves reflected by the specimen 71 are introduced to a photoconductive device 69 on the detection side through parabolic mirrors 70c and 70d.

Figure 7:
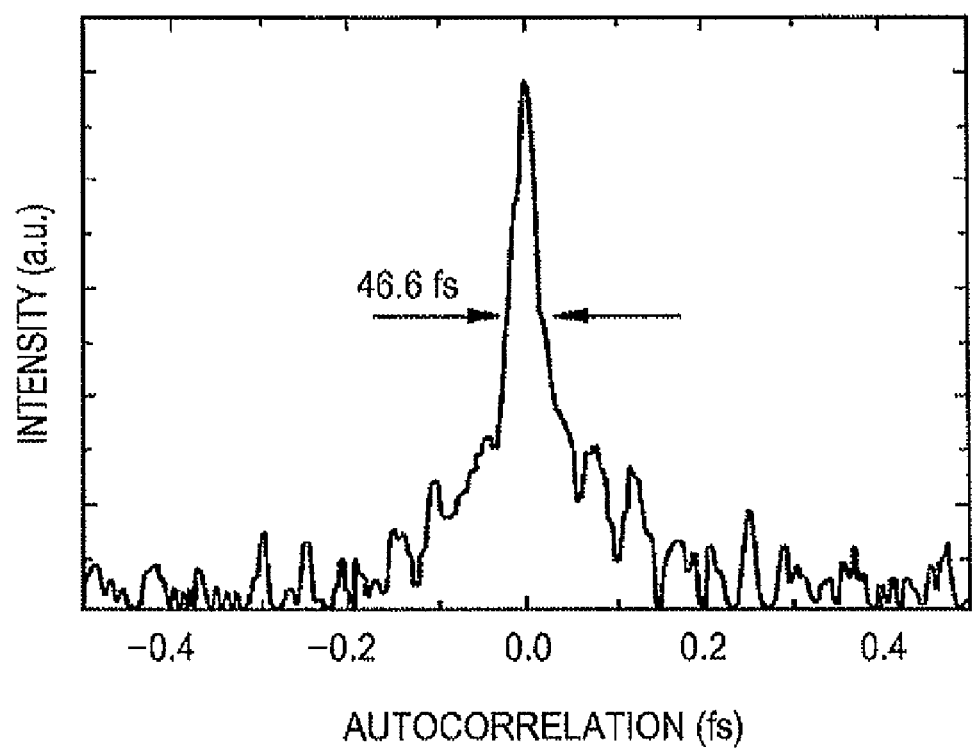
FIG. 7 is a graph representing a second harmonic wave of the pulse laser output in the first exemplary embodiment of the present invention.

In the photoconductive device 69 on the detection side, GaAs is used as a photoconductive film. For that reason, the laser beam reflected by the half mirror 61 is converted to a laser beam of 780 nm by using a waveguide-type second harmonic generator (e.g., PPLN (Periodically Poled Lithium Niobate) 64 after the direction polarization has been adjusted by a ½-wavelength plate 63. As a result of measuring a pulse width of the converted laser beam, 46.6 fs is obtained in an autocorrelation waveform shown in FIG. 7. Thus, a pulse of 780 nm in sync with the pulse of 1558 nm is obtained with a width of 30 fs in terms of time and an output of 10 mW. The second harmonic laser beam of the shorter wavelength is passed through a dichroic mirror 62 to remove light of undesired wavelengths. Thereafter, the second harmonic laser beam is introduced to enter the photoconductive device 69 on the detection side through an optical mirror 65, a delay system 66 and a condensing lens 67b.

Figure 8A:
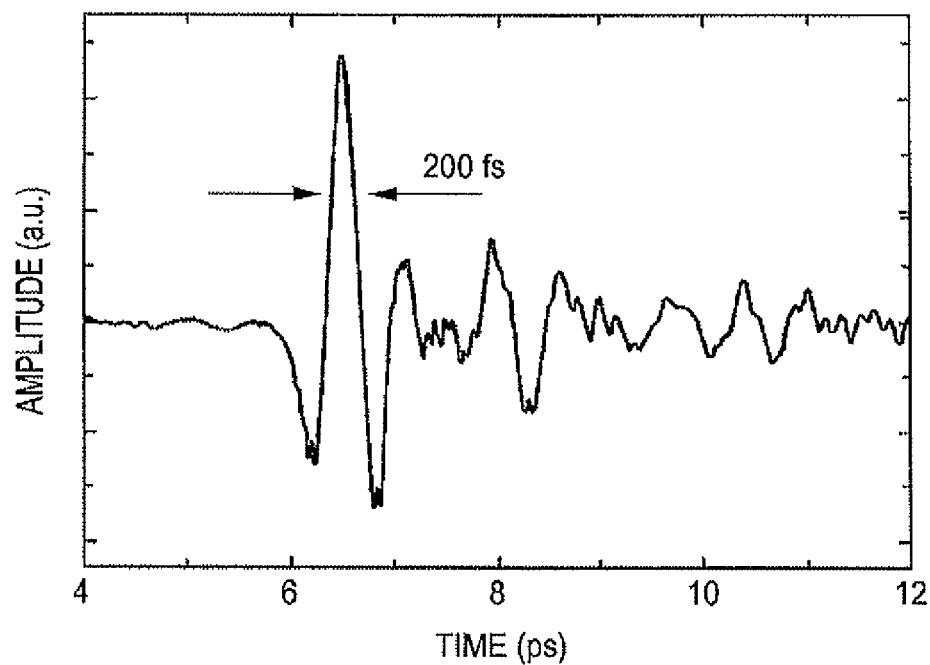
FIGS. 8A and 8B are each a graph representing a signal obtained with the terahertz TDS measuring apparatus according to the first exemplary embodiment of the present invention.
Figure 8B:
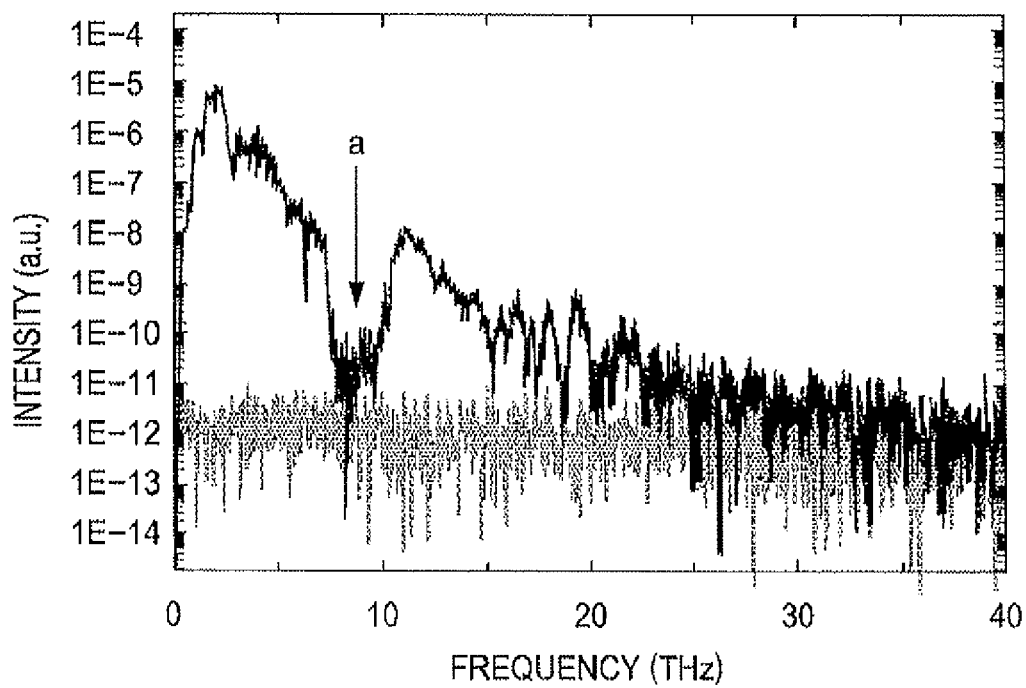

Thus, a THz-TDS system is constructed by employing, as the excitation light source, the laser beam emitted from the ultrashort pulse laser using the fiber amplifier according to the exemplary embodiment of the present invention, and by providing both the light of 1558 nm with the pulse width of 17 fs and the light of 780 nm with the pulse width of 30 fs. FIG. 8A illustrates a time-dependent waveform of THz waves obtained when a LSAT crystal is used on the THz generating side in the first exemplary embodiment, and FIG. 8b illustrates a Fourier transform spectrum of the waveform in FIG. 8A. As seen from FIG. 8A, a signal pulse with a width of 200 fs is obtained in the time-dependent waveform of the THz waves, and a signal spreading up to a band over 20 THz is obtained in the Fourier spectrum. Note that a dip, indicated by a in FIG. 8B, represents an absorption of the THz waves caused by phonons within the GaAs substrate on the detection side.

Figure 9A:
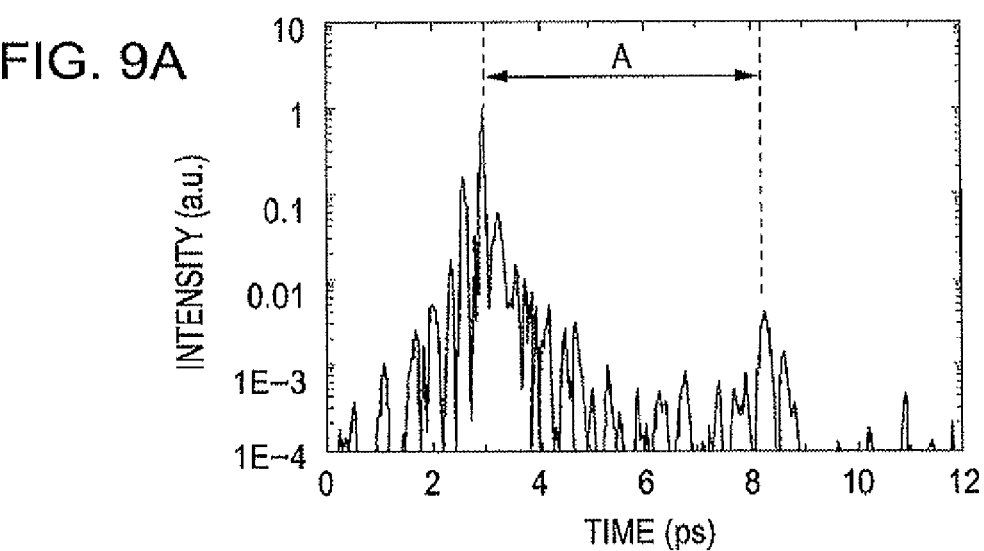
FIG. 9A is a graph and FIGS. 9B and 9C are images for explaining a tomographic image obtained with the terahertz TDS measuring apparatus according to the first exemplary embodiment of the present invention.
Figure 9B:
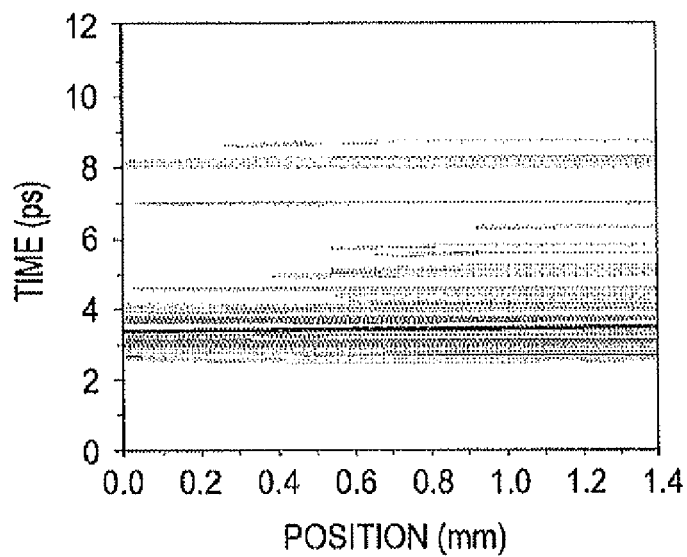
Figure 9C:
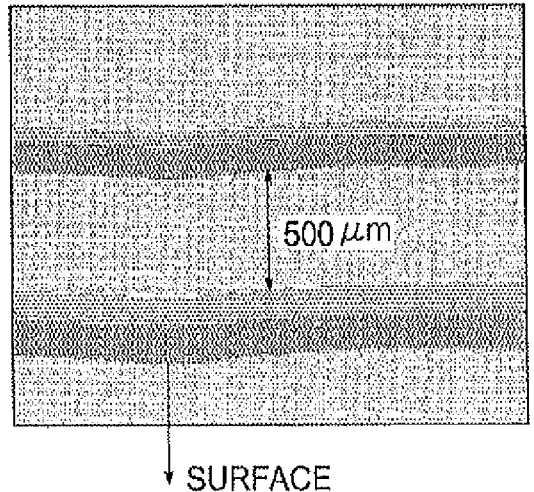

With the TDS measuring apparatus according to the first exemplary embodiment, a narrow signal pulse can be obtained in the THz-wave region and resolution in the direction of depth can be increased when a layered structure inside the specimen 71 is observed as a tomographic image. FIG. 9A is a graph and FIGS. 9B and 9C are images for explaining a tomographic image obtained when a medicine is used as the specimen. More specifically, FIG. 9C is a microscope image resulting from observing a cross-section of the medicine. A coating with a thickness of about 500 μm is applied to the surface of the medicine. FIG. 9A is a graph illustrating a part of the time-domain waveform of the signal obtained with the THz-TDS system according to the first exemplary embodiment of the present invention. As seen from FIG. 9A, the time-domain waveform includes two pulse trains, and pulses reflected by the surface and the coating interface are observed. FIG. 9B is a tomographic image formed by pulse signals which are obtained from respective points with scanning over about 1.4 mm. As seen from FIG. 9B, although several error signals are observed, an image corresponding to the microscope image of FIG. 9C is obtained. This implies that the first exemplary embodiment can provide a transmission-based tomographic image inside the specimen with no need of slicing along a cross-section. As a result of tomographic imaging according to the first exemplary embodiment, the depth resolution of about 20 μm is estimated from the time-dependent waveform of the pulse.

As described above, by constructing the THz-TDS measuring apparatus with the pulse laser apparatus according to the exemplary embodiment of the present invention, an apparatus having a high depth resolution (20 μm) and capable of providing a tomographic image of the specimen in a nondestructive manner on the transmission basis is obtained.

Second Exemplary Embodiment

A second exemplary embodiment of the present invention is constituted such that the bending radius R of the fiber amplifier is adjustable. The wavelength band, the optical power, and the spectrum band required in the THz-TDS system, according to the first exemplary embodiment, differ depending on the specifications of the measuring system. Accordingly, the degree of amplification in the fiber amplifier and the amount of optical energy in the wavelength region longer than the zero-dispersion wavelength also differ depending on the specifications of the measuring system. Further, the degree of amplification and the chirp amount differ due to a variation per lot of the erbium doped fiber.

Figure 10:
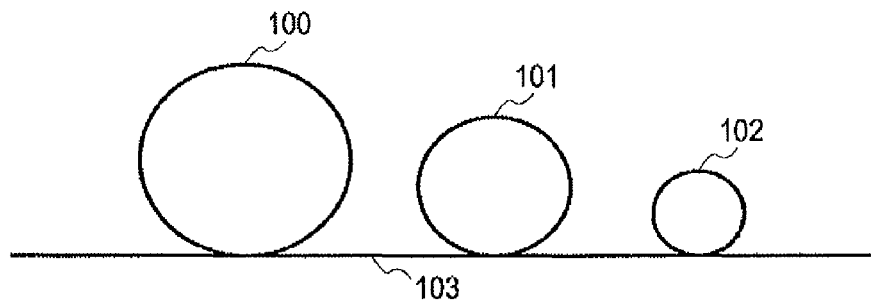
FIG. 10 illustrates a fiber amplifier according to a second exemplary embodiment of the present invention.

In this second exemplary embodiment, the curvature radius R, shown in FIG. 4B, is made variable by an actuator, for example, depending on the required optical power and pulse width. As shown in FIG. 10, a structure for winding a fiber 103 is provided as plural structures 100 to 102 having different radiuses, and one or more of the structures 100 to 102 are constructed to be movable such that the structure has a different radius.

By changing the radius of the structure, the dependency of the bending loss upon wavelength can be varied as indicated by 43a to 43c in FIG. 4A. In practice, an adjusting unit can be disposed which can set the curvature radius to an optimum range (where, for example, the pulse width is minimized and the pedestal is suppressed) while observing the light pulse waveform, shown in FIG. 5, output from the pulse compressor.

Third Exemplary Embodiment

Figure 11:
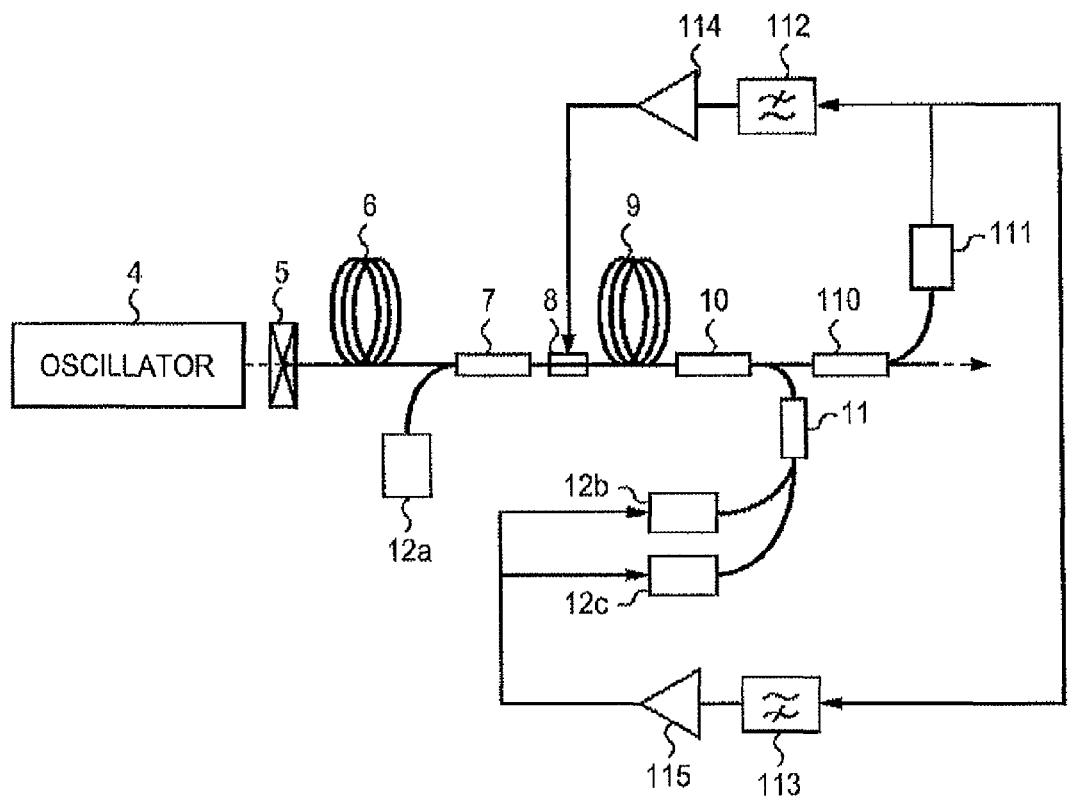
FIG. 11 illustrates a configuration of a pulse laser apparatus, particularly a fiber amplifier, according to a third exemplary embodiment of the present invention.

In a third exemplary embodiment of the present invention, a stabilizer based on feedback control is added to the fiber amplifier. In the fiber amplifier, as shown in FIG. 11, a part of the output of the erbium doped fiber is taken out by a branch unit 110. Average power of the taken-out output is monitored by a photodetector 111, and a monitored result is fed back to the polarization controller 8 and a part or all of the excitation lasers 12a to 12c. On that occasion, an output variation of the erbium doped fiber attributable to the excitation laser has a relatively quick time component (on the order of several tens minutes or shorter) in its large part, while an output variation thereof attributable to the polarization has a relatively slow time component (on the order of hour or longer) in its large part. Therefore, a low-pass filter (or an integrator) 112 is inserted into a path for a feedback signal introduced to the polarization controller 8, and a high-pass filter 113 is inserted into a path for a feedback signal introduced to the excitation laser. Respective feedback amplification rates of those feedback signals are adjusted by amplifiers 114 and 115. Instead of using the filters, equalizers (for adjusting a feedback amplification rate per signal frequency component, though not shown) can also be used to perform control in an active manner.

With the feedback control described above, the laser pulse output can be stabilized.

Fourth Exemplary Embodiment

Figure 12:
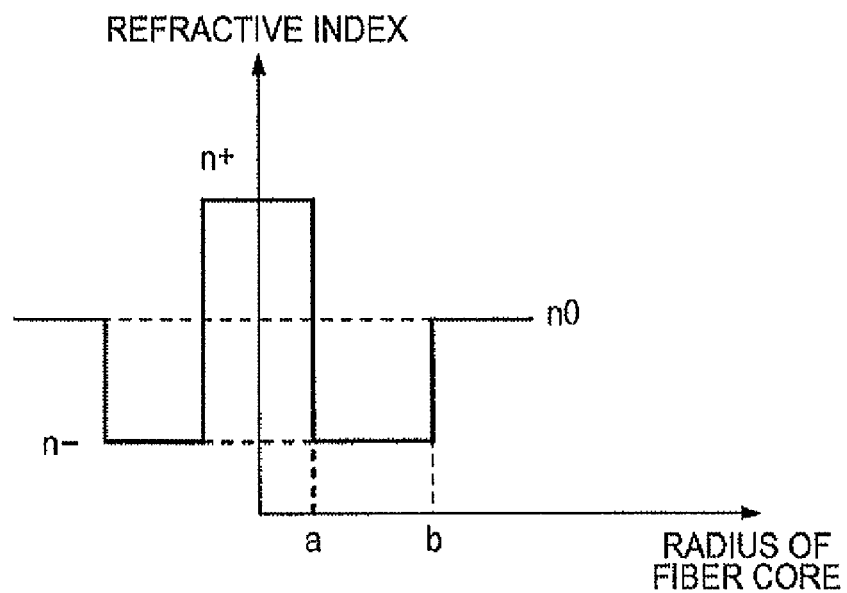
FIG. 12 is a graph representing a refractive index profile of a W-type fiber used in a fourth exemplary embodiment of the present invention.

In a fourth exemplary embodiment of the present invention, the filtering function in the longer wavelength side is improved by controlling the refractive index profile of the rare-earth doped fiber. FIG. 12 is a graph representing a W-shaped pattern of a refractive index profile of a fiber generally called the W-type.

Herein, a loss $\alpha$ in the basic mode (LP01) when the fiber is bent at the curvature radius R, is expressed by the following formula:

$$\alpha = \left(\frac{\pi v^8}{16\, aR\omega^3}\right)^{1/2} \exp\left(-\frac{4}{3}\frac{R}{a}\frac{\omega^3 \Delta}{v^2}\right)\left[\int_0^\infty \{1-f\}\frac{1}{a^2}F_0 r\, dr\right]^2 \Big/ \int_0^\infty F_0^2 \frac{1}{a^2} r\, dr \quad (1)$$

In the formula (1), a is the radius of a fiber core, which is indicated in FIG. 12, R is the curvature radius of the bending, $\omega$ is the propagation constant of an outer cladding (i.e., a portion outside a core radius b), $v$ is the normalized frequency, and $F_0$ is the intensity of an electric field. Further, f is the refractive index profile function expressed by the following formula (2), and $\Delta$ is the refractive index parameter expressed by the following formula (3).

$$f = \begin{cases} 0, & 0 < r < a \\ \dfrac{n^+ - n^-}{n^+ - n_0}, & a < r < b, \\ 1, & r > b \end{cases} \quad (2)$$

$$\Delta = \frac{1}{2}\left(1 - \frac{n_0^2}{n^{+2}}\right) \quad (3)$$

Further, the intensity $F_0$ of an electric field is determined from an electric field $E(r)$ that is expressed by the following formula (4) for each of regions shown in FIG. 12.

$$E(r) = \begin{cases} A_0 J_0(ur/a), & r < a, \\ A_1 I_0(\omega^- r/b) + A_2 K_0(\omega^- r/b), & a < r < b \\ A_3 K_0(\omega r/b), & r > b \end{cases} \quad (4)$$

In the formula (4), $J_0$, $I_0$ and $K_0$ represent respectively the Bessel function of the first kind, the modified Bessel function of the first kind, and the Bessel function of the second kind. Further, propagation constants u, $\omega^-$ and $\omega$ in the regions, shown in FIG. 12, are expressed by the following formulae (5) to (7), respectively:

$$u = a\{(k_0 n^+)^2 - \beta^2\}^{1/2} \quad (5)$$

$$\omega^- = b\{\beta^2 - (k_0 n^-)^2\}^{1/2} \quad (6)$$

$$\omega = b\{\beta^2 - (k_0 n_0)^2\}^{1/2} \quad (7)$$

In the case of the W-type fiber, the cutoff frequency (i.e., cutting of the longer wavelength side) in the basic mode can be set on the basis of the foregoing formulae without giving the bending loss. Of course, the cutoff frequency can be gradually shifted to a shorter wavelength, as shown in FIG. 4A, by changing the curvature radius R.

An example of design will be described below. It is observed that the wavelength spreads over a range of 1520 to 1650 nm due to a chirp after amplification by the above-described erbium doped fiber. Therefore, the cutoff wavelength is set to 1630 nm in order to remove extra components in the longer wavelength side. As a result, a=2 μm, b=7 μm, the radius of the fiber core=62.5 μm, $n^+$=1.4683, $n^-$=1.4520, $n_0$=1.4570 are obtained. Since this exemplary embodiment is applied to the quartz-based erbium doped fiber, the refractive index of the fiber core can be increased by controlling an amount by which germanium or aluminum is doped, and the refractive index in the inner cladding can be reduced by controlling an amount by which fluorine or boron is doped.

By using the above-described W-type fiber, dependency of the characteristics of the filter to remove the components in the longer wavelength region upon wavelength becomes sharper than the known step-index fiber. Accordingly, a propagation loss of optical energy near the zero-dispersion wavelength can be more effectively increased, and pulse compression with a smaller pedestal can be performed in the pulse compressor in the downstream stage.

Figure 13:
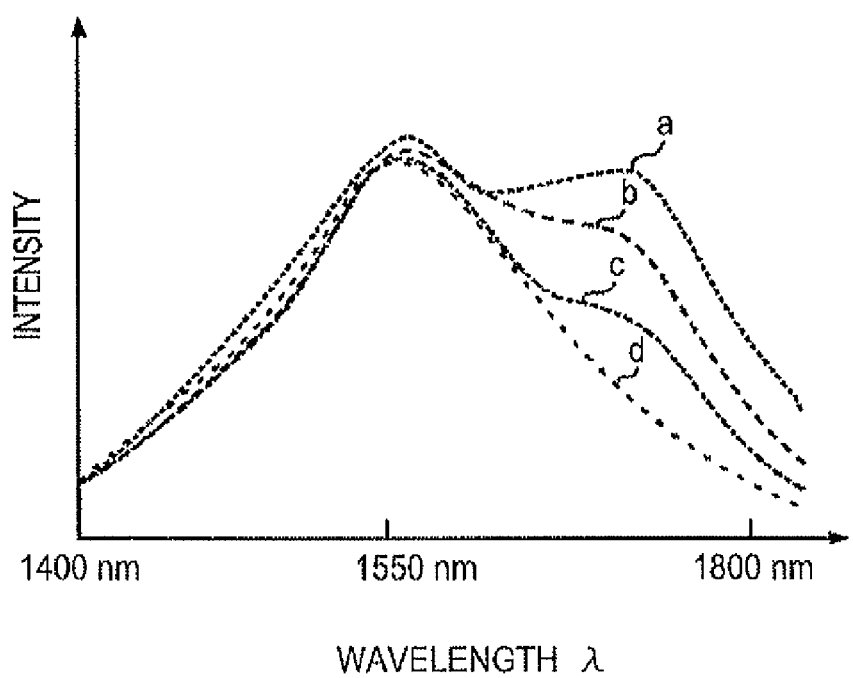
FIG. 13 is a graph for explaining the effect of bending in the fourth exemplary embodiment of the present invention.

When the fiber amplification is performed to provide a higher output, as described above regarding the related art, induced Raman scattering is generated in the longer wavelength side and nonlinear wavelength conversion is caused, whereby the pedestal tends to increase after the compression. FIG. 13 is a graph illustrating such a tendency. As seen from FIG. 13, when the W-type fiber having the cutoff frequency of 1780 nm is used, a longer wavelength component is increased, as indicated by a.

When the curvature radius is changed to 23 mm, 20 mm, and 18 mm, the cutoff frequency (assuming 3 dB with 10 m) is changed to 1720 nm, 1660 nm, and 1625 nm, respectively. It is hence understood that, as indicated by b, c and d in FIG.

13, the optical energy of the longer wavelength component, i.e., the Raman amplified component, can be reduced correspondingly. By designing the curvature radius in advance and adjusting the curvature radius while observing the wavelength spectrum, a higher output and a lower pedestal can be achieved in a well balanced manner. In general, when the induced Raman scattering occurs in the fiber amplifier, there is a threshold related to the fiber length and the optical power. Therefore, by providing the filter function to cut a longer wavelength band than the vicinity of the zero-dispersion wavelength, as described above, the optical power at the threshold can be increased and a higher power can be obtained.

Thus, since the W-type fiber can remove the undesired longer wavelength components without controlling the curvature radius, the degree of freedom in design can be increased and the attenuation characteristic as a filter can be improved. The curvature radius of the wound W-type fiber can also be changed to change the cutoff frequency, and this fourth exemplary embodiment can also be effectively applied to the case where the cutoff frequency is made variable as in the second exemplary embodiment. In some cases, the parameters determining the cutoff frequency vary due to a variation per lot in manufacturing fibers, and the cutoff frequency shifts from the designed value. In view of such a case, it is effective to practice this fourth exemplary embodiment such that the cutoff frequency is changed to the optimum value with bending of the fiber while observing the output light pulse as in the second exemplary embodiment.

While the foregoing description has been made of the erbium doped fiber for a band of 1550 nm, the exemplary embodiments of the present invention can also be similarly applied to other fiber amplifiers, such as a thulium doped fiber for a range of not lower than 1620 nm or an ytterbium doped fiber for a band of 1060 nm.

Fifth Exemplary Embodiment

A fifth exemplary embodiment is intended to further increase the performance of the TES measuring apparatus according to the first exemplary embodiment.

Figure 14:
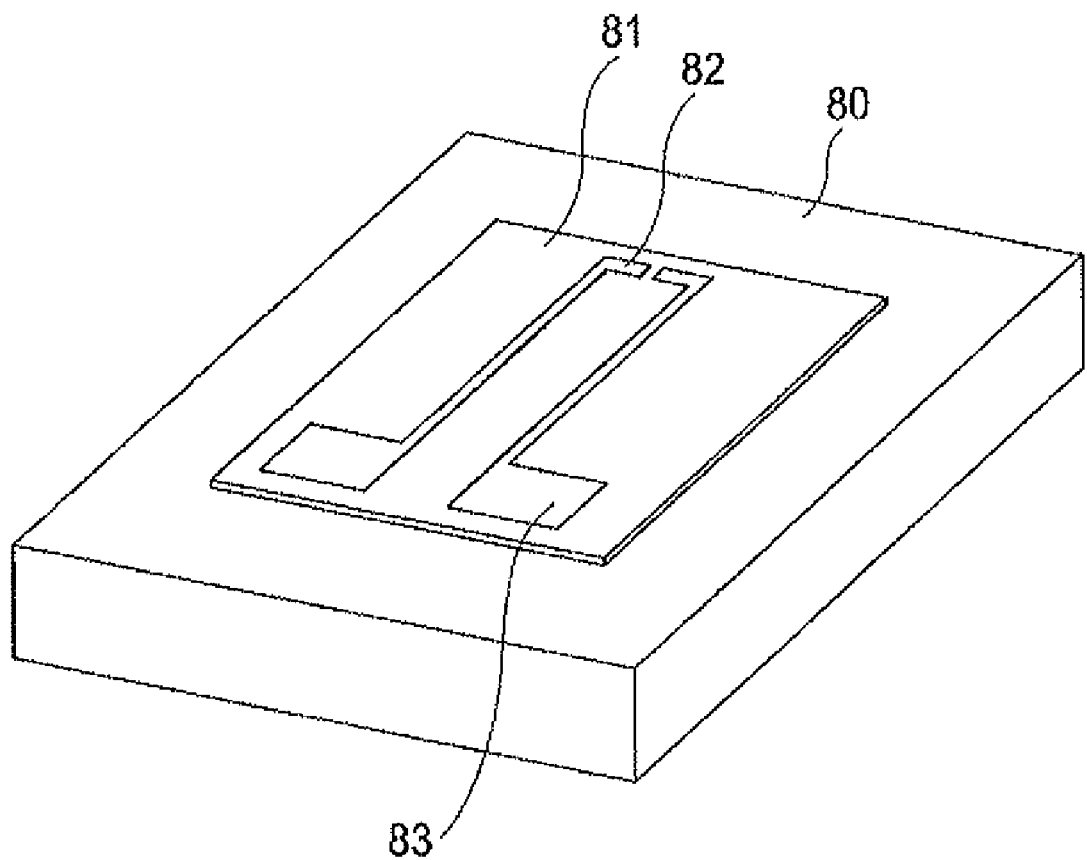
FIG. 14 illustrates a photoconductive device used in a fifth exemplary embodiment of the present invention.
Figure 15:
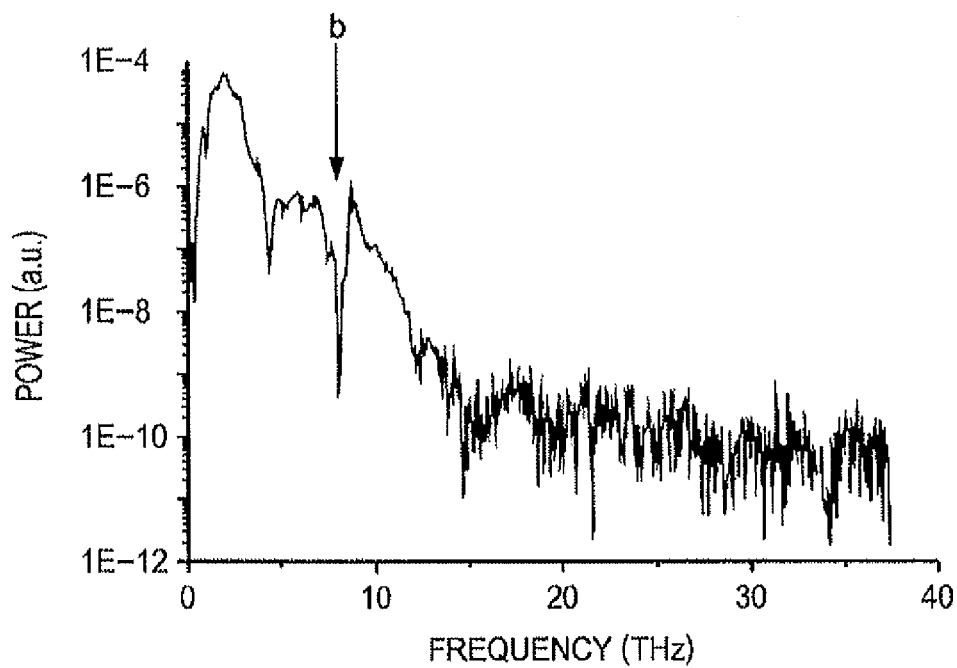
FIG. 15 is a graph representing an FFT (Fast Fourier Transform) spectrum of a signal in the fifth exemplary embodiment of the present invention.
Figure 16:
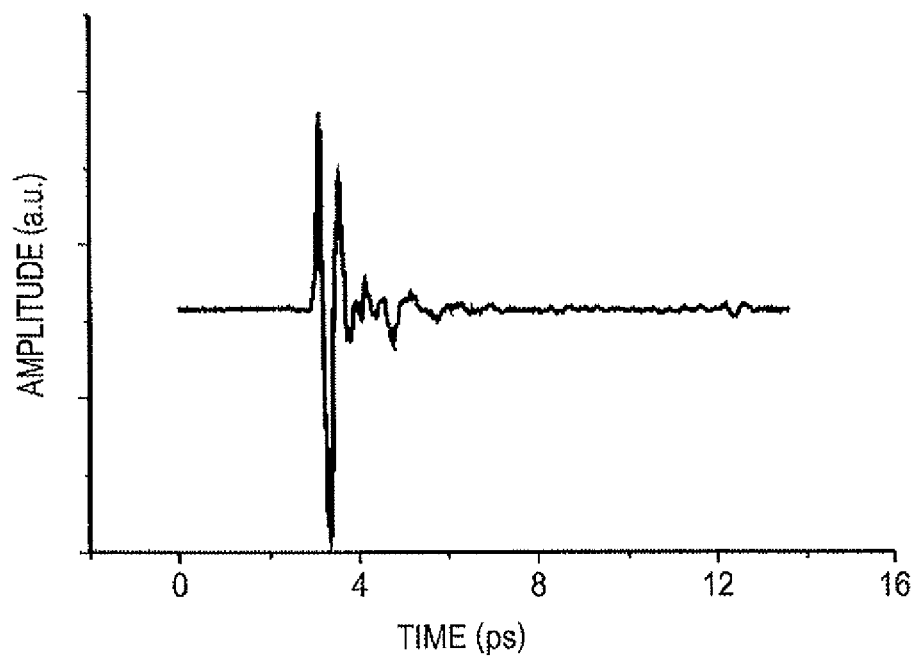
FIG. 16 is a graph representing a time-dependent waveform of the signal in the fifth exemplary embodiment of the present invention.

In order to reduce the significant phonon-caused absorption specific to GaAs, indicated by a in FIG. 8B, which is generated in the photoconductive device 69 on the detection side in the TDS measuring apparatus of FIG. 6, a photoconductive device used in this fifth exemplary embodiment has a structure that, as shown in FIG. 14, a photoconductive film 81 made of LT-GaAs is transferred onto a high-resistance Si substrate 80. Note that, in FIG. 14, numeral 82 denotes a dipole antenna portion, and 83 denotes an electrode pad for taking out a signal from the antenna portion. By using the photoconductive device according to the fifth exemplary embodiment, because the THz waves are absorbed only by the LT-GaAs film having a thickness of about 2 μm and absorption of the THz waves by the high-resistance Si substrate 80 is small, a gap b in the FFT spectrum in the range of 7 to 10 THz is greatly reduced as shown in FIG. 15. As a result, comparing with the first exemplary embodiment in which the time-dependent waveform of the THz waves includes plural pulses as shown in FIG. 8, the time-dependent waveform of the THz waves in this fifth exemplary embodiment has a single peak, as shown in FIG. 16, and an S/N ratio is increased.

Figure 17A:
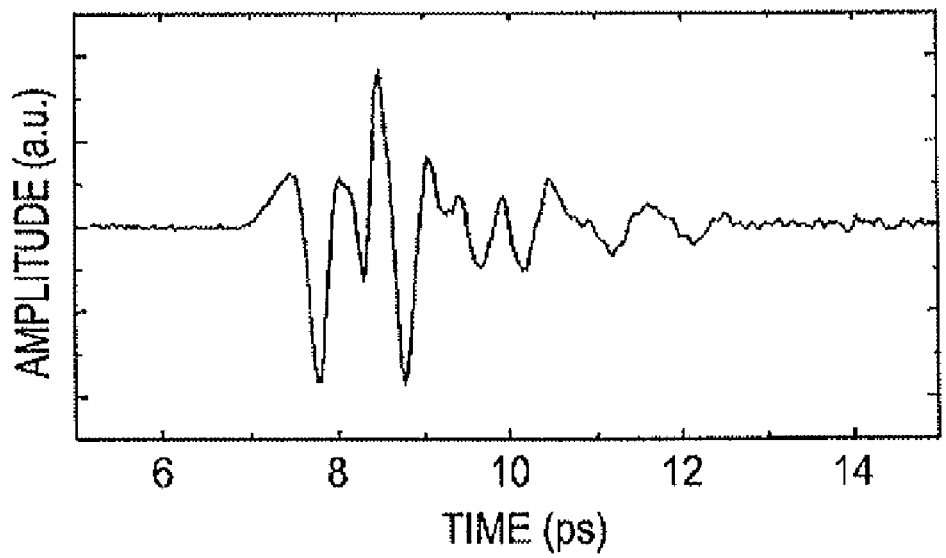
FIGS. 17A and 17B illustrate examples of reflected echo pulses.
Figure 17B:
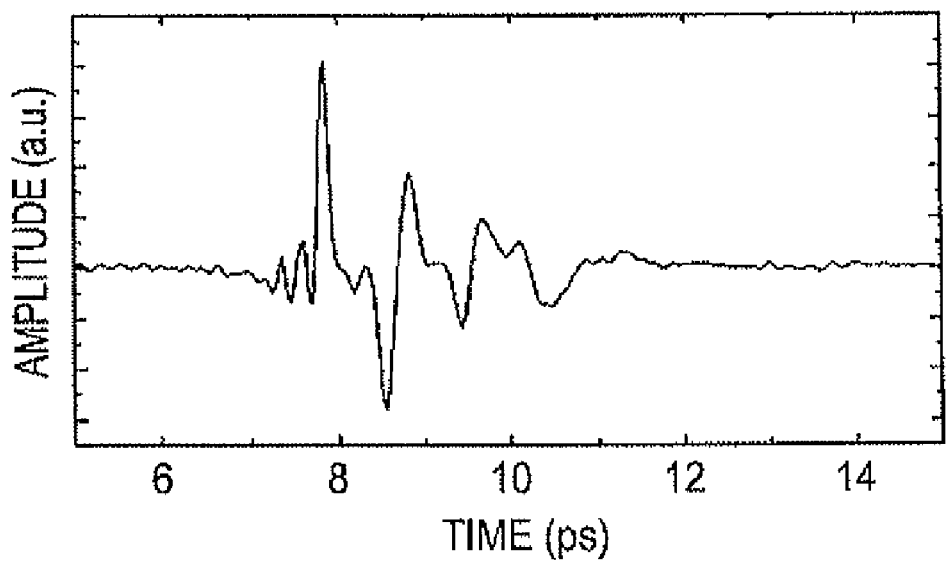
Figure 18:
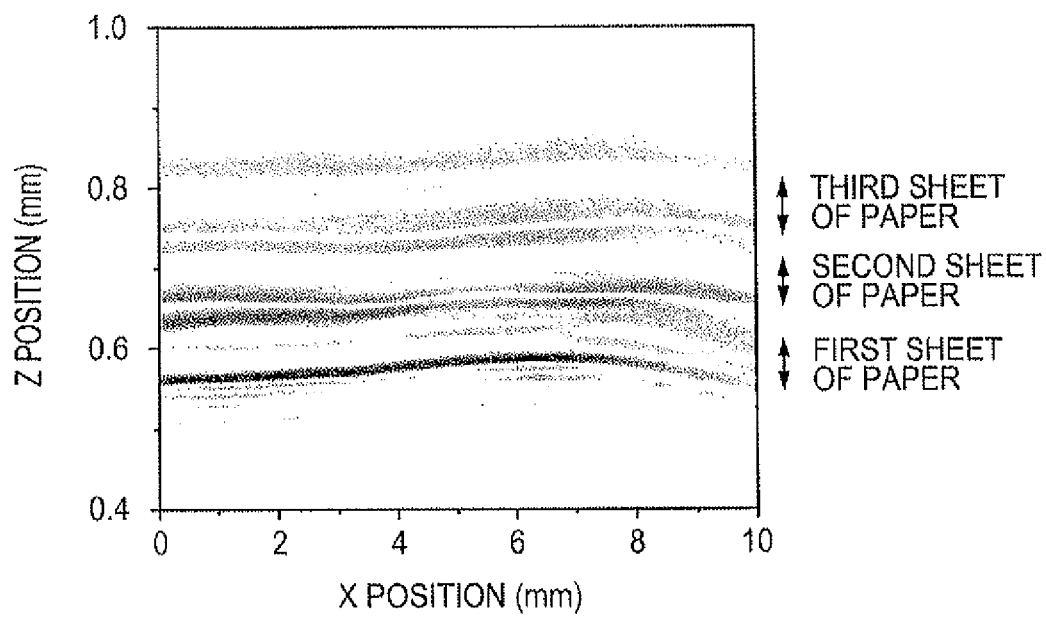
FIG. 18 illustrates an example of a tomographic image.

Further, because the THz waves are affected by water vapor in air, the waveform is changed and the resolution of a tomographic image is reduced when the measurement is performed in an environment where nitrogen purge or evacuation is not sufficient. To avoid those drawbacks, this fifth exemplary embodiment employs a deconvolution process that is a general signal processing. FIGS. 17A and 17B illustrate examples of reflected echo pulses when three sheets of paper, each having a thickness of 90 μm, are stacked one above another. FIG. 17A illustrates a waveform when the deconvolution process is not performed, and FIG. 17B illustrates a waveform when the deconvolution process is performed. As seen from FIGS. 17A and 17B, the deconvolution process enables the reflected echo peaks from respective interfaces of the three sheets of paper to be more sharply discriminated than the case not performing the deconvolution process. The deconvolution process can be performed by obtaining a reference waveform with a reflecting mirror disposed at the position of a sample (paper). FIG. 18 illustrates a tomographic image when an incident light beam is scanned over the paper sample in one direction. The state of the three sheets of paper being stacked one above another is confirmed from the tomographic image of FIG. 18.

Figure 19:
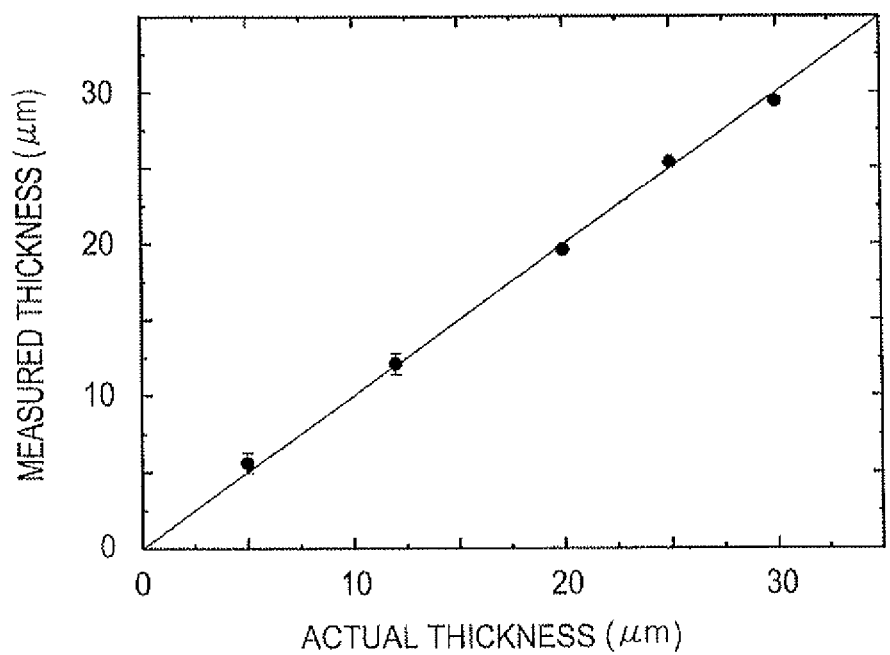
FIG. 19 is a graph representing a measured result used to estimate a thickness resolution.

In addition, to determine the depth resolution of the TDS measuring apparatus according to the exemplary embodiment of the present invention, tomographic images of Teflon sheets with various thicknesses ranging from 5 to 30 μm are obtained, and the actual thicknesses determined by a micrometer, for example, are compared with the thicknesses measured and calculated from the tomographic images obtained by the TDS measuring apparatus according to the exemplary embodiment of the present invention, as shown in FIG. 19. A linear line in the graph of FIG. 19 indicates an ideal linear line representing the relation of (actual thickness)= (measured thickness). As seen from the graph, the TDS measuring apparatus according to the exemplary embodiment of the present invention has the resolution enough to measure a thickness of about 5 μm.

Sixth Exemplary Embodiment

In this sixth exemplary embodiment, the pulse laser apparatus is constructed by using parts, which differ from those used in the foregoing exemplary embodiments. A seed light pulse generator in this sixth exemplary embodiment has an oscillation wavelength of 1561 nm, a repetition rate of 50.45 MHz, a pulse width of 506.3 fs, and an average output of 4.78 mW. Specifications of two fibers (SMF 6 and EDF 9) used in a fiber amplifier are as per listed in Table 2 given below.

TABLE 2

|  | Secondary Group Velocity Dispersion $\beta_2$ | Mode Field Diameter MFD | Length |
|---|---|---|---|
| SMF 6 | −21.9 ps$^2$/km | 10.4 μm | 10 m |
| EDF 9 | 16.8 ps$^2$/km | 6.1 μm | 6 m |

Further, in a pulse compressor, a photonic crystal fiber has the secondary group velocity dispersion of −30.3 ps$^2$/km, the mode field diameter of 26 μm, and the nonlinear coefficient of 0.182 W$^{-1}$km$^{-1}$ similarly to the above-described photonic crystal fiber, but it has the length of 200 cm. A highly nonlinear fiber has the secondary group velocity dispersion of −15.4 ps$^2$/km, the nonlinear coefficient of 4.6 W$^{-1}$km$^{-1}$, the mode field diameter of 9.4 μm, and the length of 12.4 cm.

Figure 20:
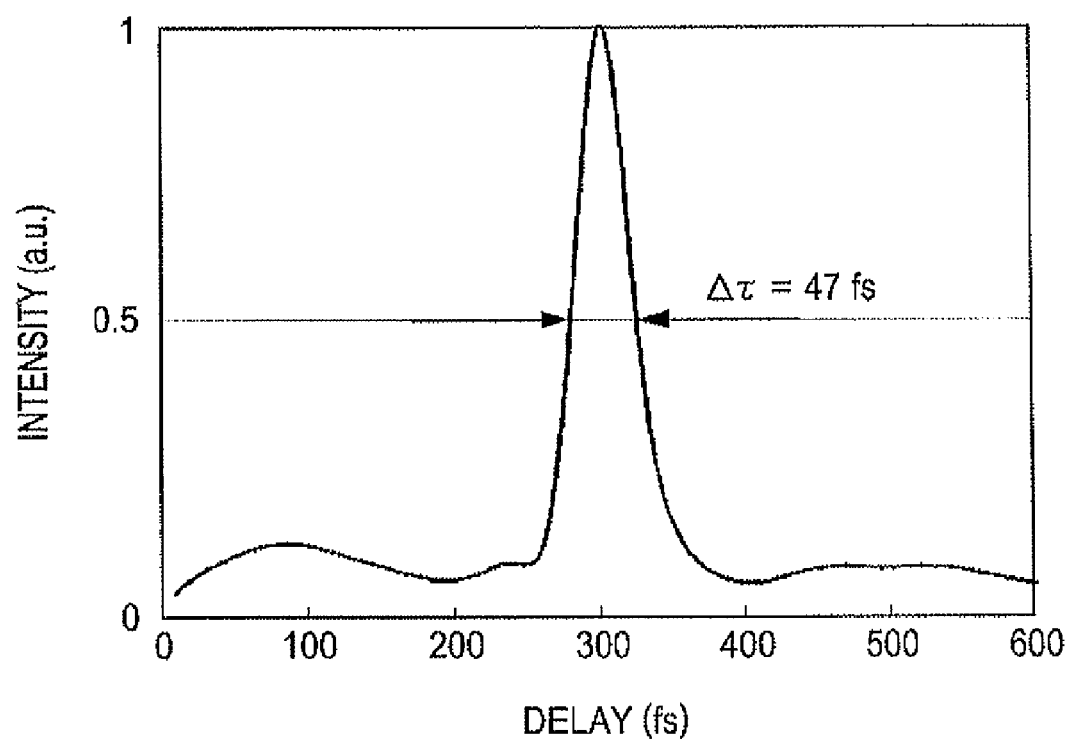
FIG. 20 is a graph representing a time-dependent waveform of a fiber laser used in a sixth exemplary embodiment of the present invention.

With such a construction, as shown in FIG. 20, the pulse width is slightly broadened and has a value of about 47 fs in the autocorrelation waveform measured by an autocorrelator or about 30 fs converted in terms of a sech$^2$ curve. The output is 134 mW. By changing characteristics of parts of the fiber, etc. in such a manner, as the occasion requires, a fiber-type pulse laser having predetermined characteristics can be obtained.

Figure 21:
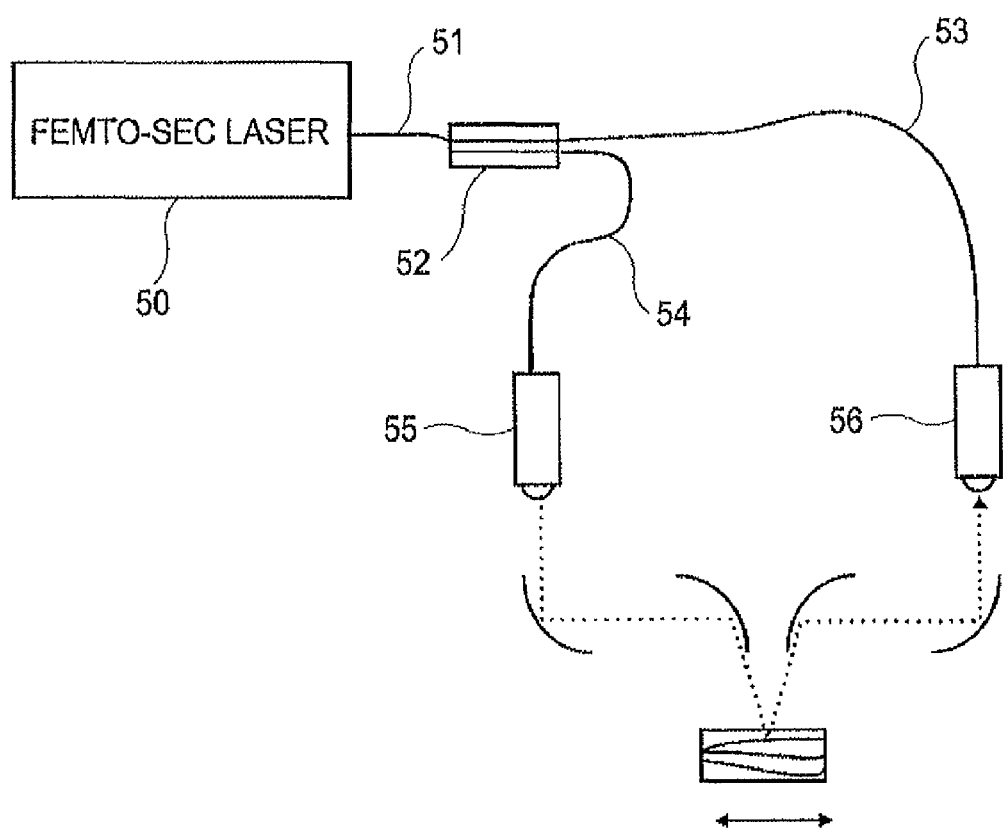
FIG. 21 illustrates a configuration of a TDS measuring apparatus according to the sixth exemplary embodiment of the present invention.

In this exemplary embodiment, as shown in FIG. 21, a TDS measuring apparatus is constructed as a fully fiber system by using the above-described fiber-type pulse laser. More specifically, an output of a femtosecond fiber laser 50 is coupled to a THz wave generator and a detector, denoted by 55 and 56, through optical fibers 51, 53 and 54 in all paths. Therefore, manual efforts for adjusting an optical axis are not required. Numeral 52 denotes a fiber coupler. Numerals 55 and 56 each represent a module integrally containing a portion for condensing a laser beam, an optical delay portion, a photoconductive device, windows for generating and detecting THz waves, and a lens for controlling directivity. In FIG. 21, an electrical system similar to that in the first exemplary embodiment is not illustrated.

The optical delay portion is incorporated in 55 or 56. The optical delay portion can be entirely formed of an optical fiber. The refractive index of a fiber medium is changed by changing an electric field or a temperature, thus causing a propagation delay. Alternatively, a fiber grating, for example, can also be used to adjust the delay time for each frequency.

When the pulse laser apparatus is fully constructed of fibers as in this sixth exemplary embodiment, a smaller and cheaper apparatus can be obtained in comparison with the pulse laser apparatus using the spatial optical system, and laborious work, such as optical adjustment, is no longer required.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2008-017842 filed Jan. 29, 2008, which is hereby incorporated by reference herein in its entirety.

What is claimed is:

1. A pulse laser apparatus comprising:
   a fiber amplifier configured to amplify and chirp a light pulse from a laser; and
   a pulse compressor configured to compress a pulse width of the light pulse from the fiber amplifier,
   wherein the fiber amplifier includes a rare-earth doped fiber that exhibits normal dispersion at a center wavelength of a wavelength spectrum of the light pulse from the laser,
   wherein the rare-earth doped fiber chirps the light pulse so that the light pulse has energy portions in a wavelength region longer than a zero-dispersion wavelength of the rare-earth doped fiber, and
   wherein the fiber amplifier is configured to give a loss to the energy portions.

2. The pulse laser apparatus according to claim 1, wherein the fiber amplifier includes a wavelength filter configured to give the loss to the energy portions.

3. The pulse laser apparatus according to claim 1, wherein the rare-earth doped fiber has, at least in a part thereof, a bent portion so that the rare-earth doped fiber gives the loss to the energy portions.

4. The pulse laser apparatus according to claim 1, wherein the rare-earth doped fiber has, at least in a part thereof, a W-shaped sectional refractive-index profile so that the rare-earth doped fiber gives the loss to the energy portions.

5. The pulse laser apparatus according to claim 1, wherein the fiber amplifier suppresses a higher-order nonlinear effect generated during propagation of the light pulse through the rare-earth doped fiber by giving the loss to the energy portions.

6. The pulse laser apparatus according to claim 1, wherein a light pulse generated by the pulse laser apparatus has a pulse width of 20 fs or less and an average output of 200 mW or more.

7. The pulse laser apparatus according to claim 5, wherein the higher-order nonlinear effect is a phenomenon of four-wave mixing.

8. The pulse laser apparatus according to claim 5, wherein the higher-order nonlinear effect is induced Raman scattering.

9. The pulse laser apparatus according to claim 3, wherein a curvature of the bent portion is variable, and the pulse laser apparatus includes a unit configured to adjust the curvature of the bent portion while monitoring a waveform.

10. A terahertz pulse generating apparatus including:
    a photoconductive device or a nonlinear crystal; and
    the pulse laser apparatus according to claim 1,
    wherein a terahertz pulse is generated by irradiating a laser beam from the pulse laser apparatus to the photoconductive device or the nonlinear crystal.

11. A terahertz measuring apparatus including:
    the laser apparatus according to claim 1; and
    a branch unit arranged to branch an optical output of the pulse laser apparatus into two parts,
    wherein one part of the optical output is irradiated to a first photoconductive device or a first nonlinear crystal to generate a terahertz pulse, and the other part of the optical output is irradiated to a second photoconductive device or a second nonlinear crystal such that the second photoconductive device or the second nonlinear crystal operates as a detector, thus performing terahertz time domain spectroscopy in accordance with pump-probe measurement.

12. The terahertz measuring apparatus according to claim 11, wherein light irradiated to the second photoconductive device or the second nonlinear crystal is obtained by passing the laser beam output from the pulse laser apparatus through a higher-harmonic generator and taking light having passed through the higher-harmonic generator as the irradiated light.

13. A terahertz tomographic apparatus wherein internal tomographic image data of a specimen is obtained by measuring a reflected pulse from the specimen with the terahertz measuring apparatus according to claim 11, and an internal tomographic image is output to an output unit on the basis of the obtained data.

14. A terahertz tomographic apparatus wherein resolution in a direction of depth is 5 μm or less when internal tomographic image data of a specimen is obtained by measuring a reflected pulse from the specimen with the terahertz measuring apparatus according to claim 11.

* * * * *